United States Patent
Hussein

(10) Patent No.: US 9,610,295 B2
(45) Date of Patent: Apr. 4, 2017

(54) METHOD FOR TREATING ERECTILE DYSFUNCTION

(71) Applicant: Hany Hussein, Costa Mesa, CA (US)

(72) Inventor: Hany Hussein, Costa Mesa, CA (US)

( * ) Notice: Subject to any disclaimer, the term of this patent is extended or adjusted under 35 U.S.C. 154(b) by 0 days.

(21) Appl. No.: 15/085,304

(22) Filed: Mar. 30, 2016

(65) Prior Publication Data

US 2016/0206630 A1    Jul. 21, 2016

Related U.S. Application Data

(60) Continuation-in-part of application No. 14/092,330, filed on Nov. 27, 2013, now abandoned, which is a division of application No. 13/065,128, filed on Mar. 15, 2011, now abandoned.

(60) Provisional application No. 61/340,303, filed on Mar. 15, 2010.

(51) Int. Cl.
| | | |
|---|---|---|
| *A61K 31/573* | (2006.01) |
| *A61K 31/519* | (2006.01) |
| *A61K 31/4985* | (2006.01) |
| *A61K 31/53* | (2006.01) |
| *A61K 9/00* | (2006.01) |
| *A61K 45/06* | (2006.01) |

(52) U.S. Cl.
CPC .......... *A61K 31/573* (2013.01); *A61K 9/0053* (2013.01); *A61K 31/4985* (2013.01); *A61K 31/519* (2013.01); *A61K 31/53* (2013.01); *A61K 45/06* (2013.01)

(58) Field of Classification Search
None
See application file for complete search history.

(56) References Cited

PUBLICATIONS

Parenting Weekly (available online at www.parentingweekly.com/preconception/preconception_information/drugs_that_may_affect_fertility.htm as of, at least, May 23, 2008).*
Coward et al (Therapeutics and Clinical Risk Management 4:1315-1329, 2008).*

* cited by examiner

*Primary Examiner* — Craig Ricci
(74) *Attorney, Agent, or Firm* — Olson & Cepuritis, Ltd.

(57) ABSTRACT

Erectile dysfunction in a male human patient is ameliorated by oral administration to the patient of a glucocorticoid such as prednisone, prednisolone, cortisone, hydrocortisone, or methylprednisolone and a phosphodiesterase type 5 (PDE5) inhibitor, such as sildenafil, vardenafil, or tadalafil.

1 Claim, No Drawings

METHOD FOR TREATING ERECTILE DYSFUNCTION

CROSS-REFERENCE TO RELATED APPLICATIONS

This application is a continuation-in-part of U.S. patent application Ser. No. 14/092,330, filed on Nov. 27, 2013, which is a division of U.S. patent application Ser. No. 13/065,128, filed on Mar. 15, 2011, and claims the benefit of U.S. Provisional Application Ser. No. 61/340,303, filed on Mar. 15, 2010. The aforementioned applications are incorporated herein by reference in their respective entireties.

FIELD OF INVENTION

This invention relates to compositions, dosage forms and methods for treating erectile dysfunction in human patients. More particularly, this invention relates to compositions comprising a phospodiesterase type 5 (PDE5) inhibitor and a glucocorticoid as well as to the use of such compositions.

BACKGROUND OF INVENTION

An erection in a human male occurs as a result of a coordinate vascular event in the penis. This event is triggered neurally and involves vasodilation and smooth muscle relaxation in the penis and its supply arterial vessels. Arterial blood inflow causes enlargement of the substance of the corpora cavernosa. Venous outflow is trapped by this enlargement, permitting sustained high blood pressures in the penis sufficient to cause and maintain rigidity. Muscles in the perineum also assist in creating and maintaining penile rigidity. Erections are induced centrally in the nervous system by sexual thoughts, fantasy, and/or stimulation, and can be reinforced locally by reflex mechanisms (e.g., tactile stimulation).

Impotence or male erectile dysfunction is an inability to achieve and sustain an erection sufficient for satisfactory sexual performance and intercourse. Impotence in any given case can result from psychological disturbances (psychogenic), from physiological abnormalities in general (organic), from neurological disturbances (neurogenic), hormonal deficiencies (endocrine) or from a combination of the foregoing factors.

Psychogenic impotence is defined as functional impotence with no apparent overwhelming organic basis. It may be characterized by an ability to have an erection in response to some stimuli (e.g., masturbation, spontaneous nocturnal, spontaneous early morning, video erotica, etc.) but not others (e.g., partner or spousal attention).

During normal penile erections, when the inflow of blood to the corpora cavernosa engages the sinusoidal spaces, the trabecular tissue compresses small cavernosal veins against the thick fibrous tissue surrounding the corpora to maintain the erection. To mediate these changes in blood flow, nitric oxide is released from postsynaptic parasympathetic neurons and, to a lesser extent, endothelial cells, and α-adrenergic neurons are inhibited in the arterial and trabecular smooth muscle. Nitric oxide, which is readily diffusible, stimulates the formation of increased cyclic guanosine monophosphate (GMP) in the corpus cavernosum by guanylate cyclase to relax the smooth muscle cells.

Oral use of certain phospodiesterase type 5 (PDE5) inhibitors has been approved by the U.S. Food and Drug Administration (FDA) for the treatment of male erectile dysfunction. Sildenafil, vardenafil and tadalafil are reported to be selective inhibitors of cyclic-GMP-specific phosphodiesterase type 5 (PDE5), the predominant isozyme metabolizing cyclic GMP formed in the corpus cavernosum. These inhibitors of PDE5 in the corpus cavernosum are believed to enhance the effect of nitric oxide, thereby increasing cavernosal blood flow in the penis, especially with sexual stimulation.

While increasing doses of the PDE5 inhibitors increased their erectogenic efficacy, the oral administration of these compounds is also accompanied by dose-responsive undesirable side effects. Consequently, higher dosages can increase to incidence of such side effects as abnormal vision problems ranging from blue or green halo effects to blurring, dyspepsia, nasal congestion, blinding headaches, flushing redness, diarrhea, dizziness, rash, and urinary tract infection increases.

Other more serious side effects have been reported, such as syncope (loss of consciousness), priapism (erection lasting 4 hours or more) and increased cardiac risk (coital coronaries), can be brought on in some cases by physiological predisposition, adverse drug interaction or potentiation, or by drug abuse. In particular, hypotension crisis can result from the combination of sildenafil citrate and organic nitrates, causing, in some cases death, so its administration to patients who are concurrently using organic nitrates (such as nitroglycerin) in any form is contraindicated. Moreover, the long-term effects of large doses of sildenafil containing drugs is not known. See, for example, Handy B., "The Viagra™ Craze," Time, pp 50-57 (May 4, 1998).

Thus, there is an ongoing need and desire for a discreet, convenient treatment of sexual dysfunction in humans, and preferably for oral delivery systems, without the incidence or likelihood of undesirable attendant side effects. It has now been found that co-administration of a glucocorticoid with the PDE5 inhibitor enhances erectogenic efficacy.

SUMMARY OF INVENTION

Compositions of the present invention, containing a PDE5 inhibitor and a glucocorticoid enhance the erectogenic efficacy of the PDE5 inhibitor, thereby permitting use of a relatively smaller amount of the PDE5 inhibitor to achieve the desired effect.

In particular, the present pharmaceutical oral dosage forms are suitable for the amelioration of male erectile dysfunction and comprise a phophodiesterase type 5 (PDE5) inhibitor which is a member of the group consisting of sildenafil, vardenafil and tadalafil together with a glucocorticoid such as prednisone, prednisolone, cortisone, hydrocortisone, triamcinolone, methylprednisolone, and the like.

Preferred active ingredients for the present compositions in addition to prednisone are sildenafil citrate, vardenafil hydrochloride and tadalafil.

The glucocorticoid and the PDE5 inhibitor can be co-administered as a single oral dosage form, or administered sequentially as separate oral dosage forms prior to sexual activity.

A preferred method of treating erectile dysfunction in a male human patient comprises orally administering to said patient 5 to 10 milligrams prednisone one to two hours prior to orally administering to the patient an effective amount of a PDE5 inhibitor which is a member of the group consisting of sildenafil, vardenafil and tadalafil.

DESCRIPTION OF PREFERRED EMBODIMENTS

The active ingredients of the oral dosage forms embodying the present invention are the PDE5 inhibitors and the glucocorticoids. The oral dosage forms can be tablets, capsules and the like, containing a PDE5 inhibitor and a glucocorticoid, and can contain conventional excipients for such dosage forms as well.

The term "effective amount" as used herein and in the appended claims refers to that amount of PDE5 inhibitor that is sufficient to achieve the intended erectogenic effect. The term also applies to a dose that will induce an erectogenic response by the patient.

The PDE5 inhibitors are sildenafil and its physiologically tolerable salt forms, vardenafil and its physiologically tolerable salt forms, and tadalafil.

Sildenafil is designated chemically as 1-[[3-(6,7-dihydro-1-methyl-7-oxo-3-propyl-1H-pyrazolo[4,3-d]pyrimidin-5-yl)-4-ethoxyphenyl]sulfonyl]-4-methyl piperazine.

The term "sildenafil" as used herein includes the free base form of this compound as well as pharmacologically acceptable acid addition salts thereof formed with organo-carboxylic acids, organo-sulphonic acids or inorganic acids. For purposes of the present invention, the organo-carboxylic acid salt, sildenafil citrate, having a solubility in water of 3.5 mg/ml, is particularly preferred. Reference to "sildenafil" includes sildenafil citrate as well as other physiologically tolerable salts thereof.

Sildenafil citrate is presently the active ingredient of a commercial medication for impotence sold under the designation Viagra® and formulated in tablets equivalent to 25 mg, 50 mg and 100 mg sildenafil for oral administration. According to the manufacturer, in addition to the active ingredient, sildenafil citrate, each tablet contains the following excipients, microcrystalline cellulose, anhydrous dibasic calcium phosphate, croscarmellose sodium, magnesium stearate, hydroxypropyl methylcellulose, titanium dioxide, lactose, triacetin, and FD&C Blue #2 aluminum lake.

It is known from in vitro studies that sildenafil is approximately 4,000 fold more selective for inhibiting phosphodiesterase type 5 (PDE5) than on other known phosphodiesterases, such as PDE3, which is involved in control of cardiac contractility. Sildenafil is reportedly only about 10-fold as potent for PDE5 compared to PDE6, an enzyme found in the retina and it is this lower selectivity which is thought to be the basis for abnormalities related to color vision observed with higher doses or plasma levels.

Sildenafil, administered as the commercially available Viagra® formulation, is reported to be rapidly absorbed after oral administration, with absolute bioavailability of about 40%. Its pharmacokinetics are dose-proportional over the recommended dose range. Based on the manufacturer's product literature, maximum observed plasma concentrations are reached within 30 to 120 minutes (median 60 minutes) of oral dosing in the fasted state. When the Viagra® formulation is taken with a high fat meal, the rate of absorption is reduced, with a mean delay in Tmax of 60 minutes and mean reduction in Cmax of 29%. The mean steady state volume of distribution (Vss) for sildenafil is reportedly 105 L, indicating distribution into the tissues. Based upon reported measurements of sildenafil in the semen of healthy volunteers 90 minutes after dosing, less than 0.001% of the administered dose appeared in the semen of the patients.

Oral combination dosage forms preferably contain a glucocorticoid in the range of about 2 to about 10 milligrams (mg), preferably in the range of about 3 to about 6 mg, and of sildenafil in the range of about 25 to about 100 mg, preferably in the range of about 25 to about 50 mg, so long as the combined dose received by the patient is accompanied by minimal or substantially no undesirable side effects. A particularly preferred sublingual combination dosage contains about 5 mg to 10 mg glucocorticoid, and about 50 mg sildenafil, more preferably about 5 mg glucocorticoid and about 25 mg sildenafil.

In a method aspect of the invention, the PDE5 inhibitor and the glucocorticoid can be administered together as a single dose or as two separate doses. For example, sildenafil and glucocorticoid each is administered in a separate dosage unit containing a lesser dosage amount of PDE5 inhibitors than is required for achieving the same level of erectile response when the PDE5 inhibitor is the sole medicament. For sequential administration of sildenafil, the dosage unit preferably contains sildenafil in a range of about 25 to about 100 mg, more preferably in the range of about 25 to about 50 mg, and for administration of glucocorticoid the dosage unit preferably contains glucocorticoid in a range of about 2 to about 10 mg, more preferably in the range of about 3 to about 6 mg so long as the total combined dose received by the patient is accompanied by minimal or substantially no undesirable side effects.

Preferably, each drug is administered sublingually. Alternatively, each drug can be administered by different oral routes; i.e., one can be ingested and the other administered sublingually or by a buccal patch.

Preferably, sublingual dosage forms dissolve within a time period of at least about 2 minutes but less than about 10 minutes. The dissolution time can be longer, however, if desired as long as the necessary plasma concentration of apomorphine and sildenafil can be maintained. More preferably, the dissolution time in water for the presently contemplated dosage forms is about 3 minutes to about 5 minutes.

Vardenafil is designated chemically as 4-[2-ethoxy-5-(4-ethylpiperazin-1-yl)-sulfonyl-phenyl]-9-methyl-7-prophyl-3,5,6,8-tetrazabicyclo[4.3.0]nona-3,7,9-trien-z-one, commercially available under the designation Levitra® as the hydrochloride salt. Vardenafil is closely related in function to as well as in structure to sildenafil.

Oral combination dosage forms preferably contain a glucocorticoid in the range of about 2 to about 10 mg, preferably in the range of about 3 to about 6 mg, and of vardenafil in the range of about 2.5 mg to about 20 mg, preferably in the range of about 3 mg to about 15 mg, so long as the combined dose received by the patient is accompanied by minimal or substantially no undesirable side effects. A particularly preferred sublingual combination dosage contains about 5 mg of glucocorticoid and about 5 mg of vardenafil.

Tadalafil is designated chemically as (6R-trans)-6-(1,3-benzodioxol-5-yl)-2,3,6,7,12,12a-hexahydro-2-methyl-pyrazino[1,2:1,6]-pyrido[3,4-6]indole-1,4-dione, commercially available under the designation Cialis®. Like sildenafil and vardenafil, tadalafil inhibits PDE5, but provides a relatively longer half-life of about 17.5 hours as compared to sildenafil (4 to 5 hours) and vardenafil (4 to 5 hours).

Oral combination dosage forms preferably contain a glucocorticoid in the range of about 2 mg to about 10 mg, preferably in the range of about 3 mg to about 6 mg, and of tadalafil in the range of about 5 mg to about 20 mg, preferably in the range of about 5 mg to 10 mg, so long as the combined dose received by the patient is accompanied by minimal or substantially no side effects.

Glucocorticoids are a class of steroid hormones that bind to the glucocorticoid receptor which is found in vertebrate animal cells. It has now been found that glucocorticoids enhance the erectogenic properties of PDE5 inhibitors such as sildenafil, vardeuafil and tadalafil. Particularly preferred for this purpose are the short-to-medium acting glucocorticoids such as prednisone, prednisolone, cortisone, hydrocortisone (cortisol), and methyl-prednisolone.

For sildenafil, particularly preferred is a dosage comprising about 10 mg of prednisone and about 50 mg of sildenafil.

For tadalafil, particularly preferred is a dosage of about 5 to 10 mg of prednisone and about 10 mg of tadalafil.

The glucocorticoid and the PDE5 inhibitor can be administered orally to a male human patient as two separate dosages or as a single combined dosage. Preferably, prednisone is administered one to two hours prior to administration of the PDE5 inhibitor such as sildenafil, vardenafil or tadalafil. A particularly preferred method comprises oral administration of 5 to 10 mg of prednisone one to two hours prior to oral administration of 10 mg of tadalafil.

EXAMPLE 1

Co-Administration of Sildenafil and Prednisone

A 61-year old male patient (80 kg) received an oral dose of sildenafil (50 mg; Viagra®) and prednisone (5 mg) about one hour prior to sexual activity. Prior to that time, as daily maintenance therapy due to a kidney transplant, the patient had ingested an additional 5-mg dose of prednisone.

Upon onset of an erection the patient noted a marked increase in the tumescence of the glans penis and stiffness of the shaft. Introitus and successful intercourse followed.

EXAMPLE 2

Co-Administration of Tadalafil and Prednisone

A 62-year old male patient (about 80 kg) received an oral dose of tadalafil (10 mg; Cialis®) and prednisone (5 mg) about one hour prior to sexual activity. Prior to that time, as daily maintenance therapy due to a kidney transplant, the patient had ingested an additional 5-mg dose of prednisone.

Upon onset of an erection the patient noted a marked increase in the tumescence of the glans penis and stiffness of the shaft. Introitus and successful intercourse followed. No adverse events were noted.

EXAMPLE 3

Co-Administration of Vardenafil and Prednisone

A 62-year old male patient (about 80 kg) received an oral dose of vardenafil (10 mg; Levitra®) and prednisone (5 mg) about one hour prior to sexual activity. Prior to that time, as daily maintenance therapy due to a kidney transplant, the patient had ingested an additional 5-mg dose of prednisone.

Upon onset of an erection the patient noted a marked increase in the tumescence of the glans penis and stiffness of the shaft. Introitus and successful intercourse followed. No adverse events were noted.

EXAMPLE 4

Co-Administration of Tadalafil and Prednisone

A 64-year old male patient had been self-administering a daily oral dose of prednisone (5 milligrams) as a maintenance therapy due to a kidney transplant.

For a time period of about 66 months the patient self-administered an additional 5 to 10 milligrams of prednisone one to two hours prior to self-administration of PDE5 inhibitor sildenafil (50 milligrams), vardenafil (10 milligrams) or tadalafil (10 milligrams) in anticipation of intercourse. An enhanced erectogenic effect to various degrees was achieved.

Greatly enhanced erectogenic effect was achieved by self-administration of 5 to 10 milligrams of prednisone and 10 milligrams of tadalafil in the aforesaid manner.

Prior to the self-administration of additional prednisone and the PDE5 inhibitor as described hereinabove the patient's International Index of Erectile Function (IIEF) score, based on the standard test questionnaire, was 5 (a score of 5-7 being the range of severe erectile dysfunction (ED)), and was found to be 22 (a score of 22-25 being the range for no ED) as a result of self-administration of prednisone and the PDE5 inhibitor as described hereinabove.

A significant increase in the satisfaction of the patient's consort was observed as well.

The observations set forth in this Example were based on 520 patient points over a 66 month time period, a "patient point" representing data from the patient in one day.

The foregoing discussion and the Examples are illustrative of the present invention, and should not be construed as limiting. Still other variations within the scope of the claims are possible, and will readily present themselves to those skilled in the art.

I claim:

1. A method of treating erectile dysfunction in a male human patient, comprising orally administering to said patient 5 to 10 milligrams prednisone one to two hours prior to orally administering to said patient 10 milligrams tadalafil.

* * * * *